United States Patent [19]

Brändström

[11] Patent Number: 5,386,032
[45] Date of Patent: Jan. 31, 1995

[54] METHOD OF SYNTHESIS OF 5-METHOXY-2-[(4-METHOXY-3,5-DIMETHYL-2-PYRIDINYL)-METHYL]SULFINYL-1H-BENZIMIDAZOLE (OMEPRAZOLE)

[75] Inventor: Arne E. Brändström, Gothenburg, Sweden

[73] Assignee: Aktiebolaget Astra, Sodertalje, Sweden

[21] Appl. No.: 67,406

[22] Filed: May 25, 1993

Related U.S. Application Data

[63] Continuation of Ser. No. 708,345, May 31, 1991, abandoned.

[30] Foreign Application Priority Data

Jun. 7, 1990 [SE] Sweden ................. 9002043

[51] Int. Cl.6 .......................... C07D 401/00
[52] U.S. Cl. ........................... 546/271
[58] Field of Search ......................... 546/271

[56] References Cited

U.S. PATENT DOCUMENTS

| | | | |
|---|---|---|---|
| 4,182,766 | 1/1980 | Krasso | 546/271 |
| 4,255,431 | 3/1981 | Junggren et al. | 514/338 |
| 4,307,102 | 12/1981 | Bell | 514/338 |
| 4,686,230 | 8/1987 | Rainer et al. | 546/271 |
| 4,996,217 | 2/1991 | Honma et al. | 546/271 |
| 5,002,945 | 3/1991 | Honma et al. | 546/271 |

FOREIGN PATENT DOCUMENTS 0163842 12/1985 European Pat. Off. .
0197013 10/1986 European Pat. Off. .
8705021 8/1987 WIPO .

Primary Examiner—C. Warren Ivy
Assistant Examiner—Raymond Covington
Attorney, Agent, or Firm—White & Case

[57] ABSTRACT

The present invention relates to an improved method for the synthesis of omeprazole, comprising the steps of reacting 5-methoxy-2-[(4-methoxy-3,5-dimethyl-2-pyridinyl)-methylthio]-1H-benzimidazole with m-chloroperoxybenzoic acid in a methylene chloride solution at a substantially constant pH of about 8.0 to 8.6; extracting the reaction mixture with aqueous NaOH; separating the aqueous phase from the organic phase; and adding an alkyl formate to the aqueous phase, resulting in crystallization of omeprazole.

11 Claims, No Drawings

METHOD OF SYNTHESIS OF 5-METHOXY-2-[(4-METHOXY-3,5-DIMETHYL-2-PYRIDINYL)-METHYL]SULFINYL-1H-BENZIMIDAZOLE (OMEPRAZOLE)

This application is a continuation of application Ser. No. 07/708,345, filed on May 31, 1991, now abandoned.

TECHNICAL FIELD

The present invention relates to an improved method for the synthesis of 5-methoxy-2[-(4-methoxy-3,5-dimethyl-2-pyridinyl)-methyl]sulfinyl-1H-benzimidazole, referred to under its generic name omeprazole throughout the following specification and claims.

PRIOR ART

U.S. Pat. No. 4,255,431 discloses a process for the synthesis of omeprazole comprising the steps of reacting 5-methoxy-2-[(4-methoxy-3,5-dimethyl-2-pyridinyl)-methylthio]-1H-benzimidazole in a methylene chloride solution with m-chloroperoxybenzoic acid resulting in the formation of omeprazole and m-chlorobenzoic acid. omeprazole is highly sensitive to acids, and the reaction mixture has to be maintained at a low temperature to prevent excessive decomposition in the reaction mixture.

The product is worked-up by filtering-off of m-chlorobenzoic acid formed during the reaction. The filtrate is diluted with methylene chloride, is extracted with $Na_2CO_3$ solution, dried and evaporated. The resulting omeprazole product is contaminated with starting materials and byproducts.

SUMMARY OF THE INVENTION

The object of the present invention is to provide an improved method for the synthesis of omeprazole, which eliminates the drawbacks of previously known methods.

This object is achieved according to the present invention, which is characterized by the steps of reacting 5-methoxy-2-[(4-methoxy-3,5-dimethyl-2-pyridinyl)-methyl-thio]-1H-benzimidazole (below denoted Compound I) with m-chloroperoxybenzoic acid in a methylene chloride solution at a substantially constant pH of about 8.0 to 8.6; extracting the reaction with aqueous NaOH; separating the aqueous phase from the organic phase; and adding an alkyl formate to the aqueous phase, resulting in crystallization of omeprazole.

The m-chloroperoxybenzoic acid is suitably used in an amount of 0.7–1.4 molar equivalents of Compound I, and preferably in an amount of 0.9–1.2 molar equivalents.

According to one embodiment of the invention, the alkyl formate is methylformate or ethylformate, methylformate being preferred.

The alkyl formate is suitably used in an amount of 1.2–2.0 molar equivalents of Compound I, and preferably in an amount of 1.5–1.8 molar equivalents.

One important feature of the method according to the invention is that unreacted sulfide is not transferred into the aqueous phase upon the extraction with aqueous NaOH. Another important feature is that m-chlorobenzoic acid does not crystallize upon the addition of methylformate formate to the aqueous phase, thereby eliminating the need of filtering-off of m-chlorobenzoic acid in a previous step.

The pH of the reaction mixture may be maintained within the pH range of 8.0–8.6 with the aid of pH static titration with NaOH or with the use of a buffer. Preferred buffers are sodium bicarbonate and potassium bicarbonate. A great advantage of the method according to the invention is that the reaction takes place in the organic methylene chloride phase while the m-chlorobenzoic acid formed during the reaction goes into the aqueous phase containing the buffer, in the case a buffer is used. Because of this, omeprazole formed does not stay in contact with the acid and the reaction may be performed at a temperature above 0° C.

According to one embodiment of the invention the pH of the aqueous NaOH phase is kept at above about 12.

According to another embodiment of the invention the crystallization of omeprazole is performed at a pH of above 9.

The invention will be further illustrated below with a non-limiting example.

EXAMPLE 5-methoxy-2-[(4-methoxy-3,5-dimethyl-2-pyridinyl)-methylthio]-1H-benzimidazole (16.2 g; 0.0492 mol) is reacted with m-chloroperoxybenzoic acid (13.6 g; 0.0537 mol) in $CH_2Cl_2$ acting as a solvent at a pH of 8.6, which is maintained by the presence of $KHCO_3$ (5.6 g; 0.056 mol) acting as a buffer. The temperature is maintained at about 0° C. during the addition.

Diluted NaOH is added to a pH above 12 and the $CH_2Cl_2$ phase is separated off.

Methylformate (4.7 g) is charged to the water phase and the pH is kept above 9, whereupon omeprazole crystallizes. The crystals are filtered off and are washed with water and methanol at a temperature of about 0° C. The washed crystals are dried under vacuum. Yield: 15.6 g (92%).

I claim:

1. An improved method for the production of omeprazole which comprises reacting 5-methoxy-2-[(4-methoxy-3,5-dimethyl-2-pyridinyl)-methylthio]-1H-benzimidazole (Compound I) with m-chloroperoxybenzoic acid in a methylene chloride solution at a substantially constant pH of about 8.0 to 8.6; extracting the reaction mixture with aqueous NaOH; separating the aqueous phase from the organic phase; and adding an alkyl formate to the aqueous phase, resulting in the crystallization of omeprazole.

2. Method according to claim 1, wherein that the m-chloroperoxybenzoic acid is used in an amount of 0.7–1.4, molar equivalents of Compound I.

3. Method according to claim 1, wherein the alkyl formate is methylformate.

4. Method according to claim 1, wherein pH of the reaction mixture is maintained within the pH range of 8.0–8.6 with the aid of pH static titration with NaOH.

5. Method according to claim 1, wherein pH of the reaction mixture is maintained within the pH range of 8.0–8.6 with the use of a buffer.

6. Method according to claim 5, wherein the buffer is sodium bicarbonate or potassium bicarbonate.

7. Method according to claim 1, wherein the pH of the aqueous NaOH phase is kept at above about 12.

8. Method according to claim 1, wherein the alkyl formate is added in an amount of 1.2–2.0 molar equivalents of Compound I.

9. Method according to anyone of the claims 1–8, wherein the crystallization of omeprazole is performed at a pH of above 9.

10. The method according to claim 2 wherein the m-chloroperoxybenzoic acid is added in an amount of 0.9–1.2 molar equivalents of Compound I.

11. The method according to claim 8, wherein the alkyl formate is added in an amount of 1.5–1.8 molar equivalents of compound I.

* * * * *